United States Patent
Gebrian et al.

(10) Patent No.: US 6,808,304 B2
(45) Date of Patent: Oct. 26, 2004

(54) METHOD FOR MIXING LIQUID SAMPLES USING A LINEAR OSCILLATION STROKE

(75) Inventors: Peter Louis Gebrian, Wilmington, DE (US); Edward Francis Farina, Oxford, PA (US)

(73) Assignee: Dade Behring Inc., Deerfield, IL (US)

(*) Notice: Subject to any disclaimer, the term of this patent is extended or adjusted under 35 U.S.C. 154(b) by 61 days.

(21) Appl. No.: 10/228,509

(22) Filed: Aug. 27, 2002

(65) Prior Publication Data

US 2004/0042339 A1 Mar. 4, 2004

(51) Int. Cl.⁷ .............................................. B01F 11/00
(52) U.S. Cl. ........................................ 366/110; 366/212
(58) Field of Search ...................... 366/203, 108–116, 366/208–219

(56) References Cited

U.S. PATENT DOCUMENTS

| | | | | |
|---|---|---|---|---|
| 1,417,219 A | * | 5/1922 | Warren | 366/212 |
| 3,289,610 A | * | 12/1966 | Lounsbury et al. | 366/109 |
| 3,503,592 A | * | 3/1970 | Taylor et al. | 366/212 |
| 3,830,474 A | * | 8/1974 | Tannenbaum | 366/203 |
| 4,662,760 A | * | 5/1987 | Powell | 366/211 |
| 4,720,374 A | | 1/1988 | Ramachandran | |
| 5,165,205 A | * | 11/1992 | Nakagawa et al. | 451/392 |
| 5,482,861 A | | 1/1996 | Clark et al. | |
| 5,575,976 A | | 11/1996 | Choperena et al. | |
| 5,813,759 A | * | 9/1998 | Gebrian | 366/110 |
| 5,824,276 A | | 10/1998 | Janssen et al. | |
| 5,884,999 A | * | 3/1999 | Muzzio et al. | 366/219 |
| 5,988,869 A | * | 11/1999 | Davidson et al. | 366/208 |
| 6,059,446 A | * | 5/2000 | Dschida | 366/215 |
| 6,117,392 A | | 9/2000 | Hanawa et al. | |
| 6,117,683 A | | 9/2000 | Kodama et al. | |
| 6,141,602 A | | 10/2000 | Igarashi et al. | |
| 6,149,292 A | * | 11/2000 | Degrande | 366/111 |
| 6,250,792 B1 | * | 6/2001 | Krush et al. | 366/128 |
| 6,322,243 B1 | * | 11/2001 | Bull | 366/208 |
| 6,382,827 B1 | | 5/2002 | Gebrian | |
| 6,390,660 B1 | * | 5/2002 | Colin | 366/116 |
| 2001/0030906 A1 | * | 10/2001 | Friedman | 366/114 |
| 2002/0044495 A1 | * | 4/2002 | Friedman | 366/212 |
| 2003/0081499 A1 | * | 5/2003 | Friedman | 366/208 |

FOREIGN PATENT DOCUMENTS

| | | | |
|---|---|---|---|
| DE | 4102296 A1 | * | 8/1991 |
| FR | 1409780 | * | 7/1965 |
| FR | 2567416 | * | 1/1986 |
| JP | 60-5225 | * | 1/1985 |
| JP | 2002-153742 | * | 5/2002 |
| JP | 2002-361061 | * | 12/2002 |
| WO | 00/56437 | * | 9/2000 |

* cited by examiner

Primary Examiner—Charles E. Cooley
(74) Attorney, Agent, or Firm—Leland K. Jordan

(57) ABSTRACT

A method for generating a vortex-like mixing action within a liquid held in a container by causing the container to move back and forth in a constant sinusoidal pattern at high speeds. Momentum forces acting upon the liquid solution cause it to generate an internal mixing motion of the liquid solution without the aid of extraneous mixing members.

9 Claims, 11 Drawing Sheets

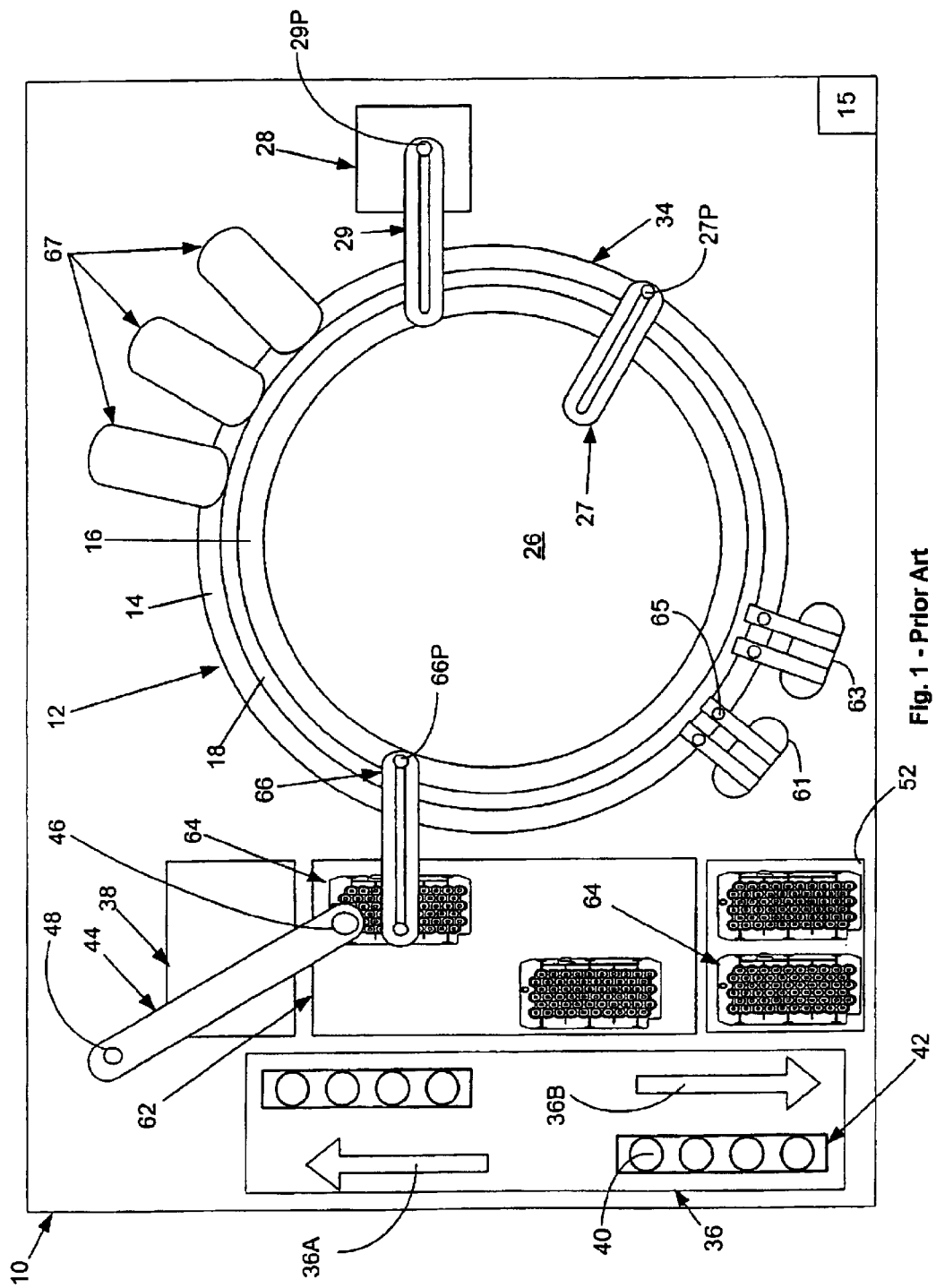
Fig. 1 - Prior Art

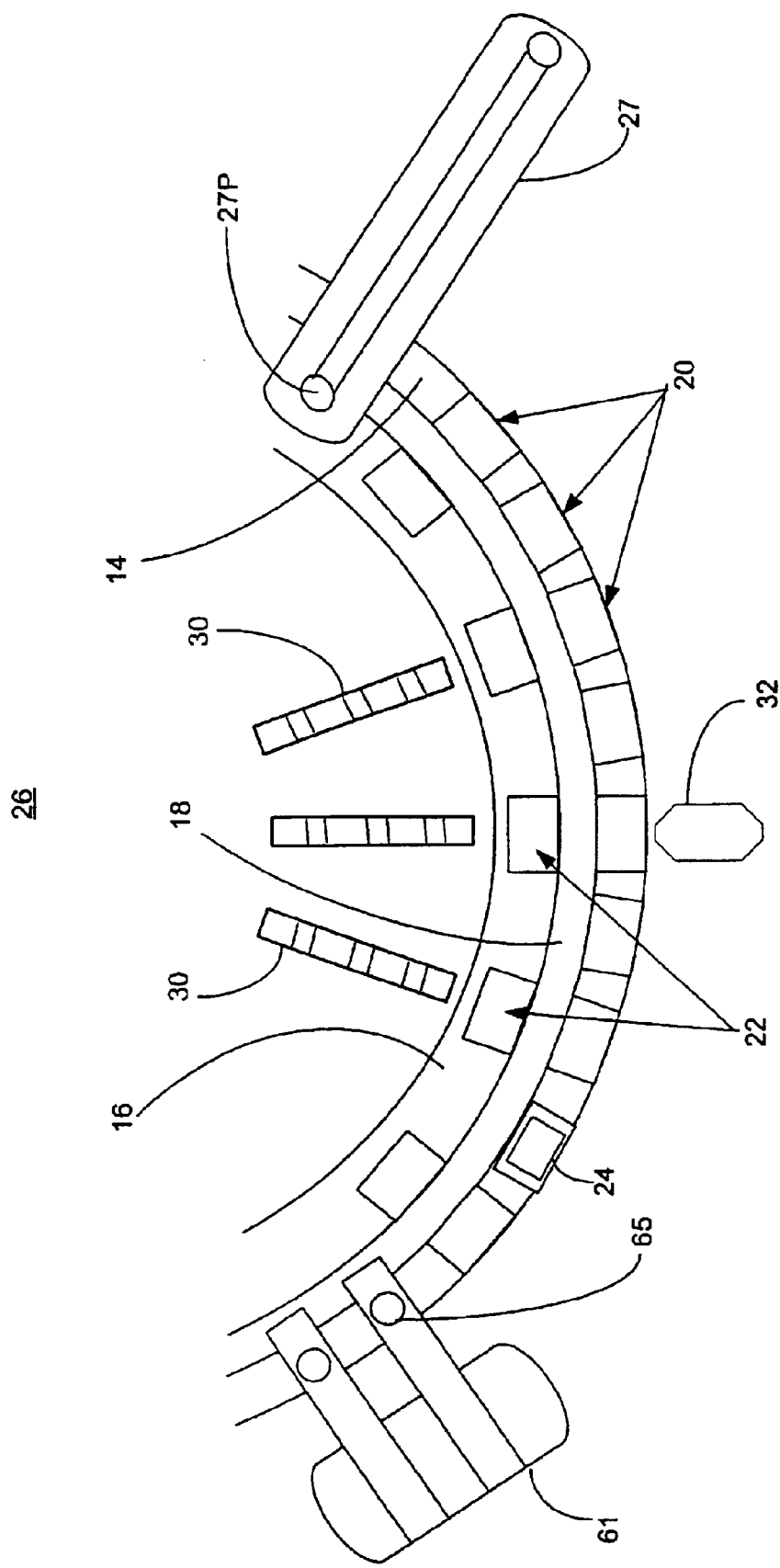
Fig. 2 - Prior Art

Fig. 5 - Prior Art

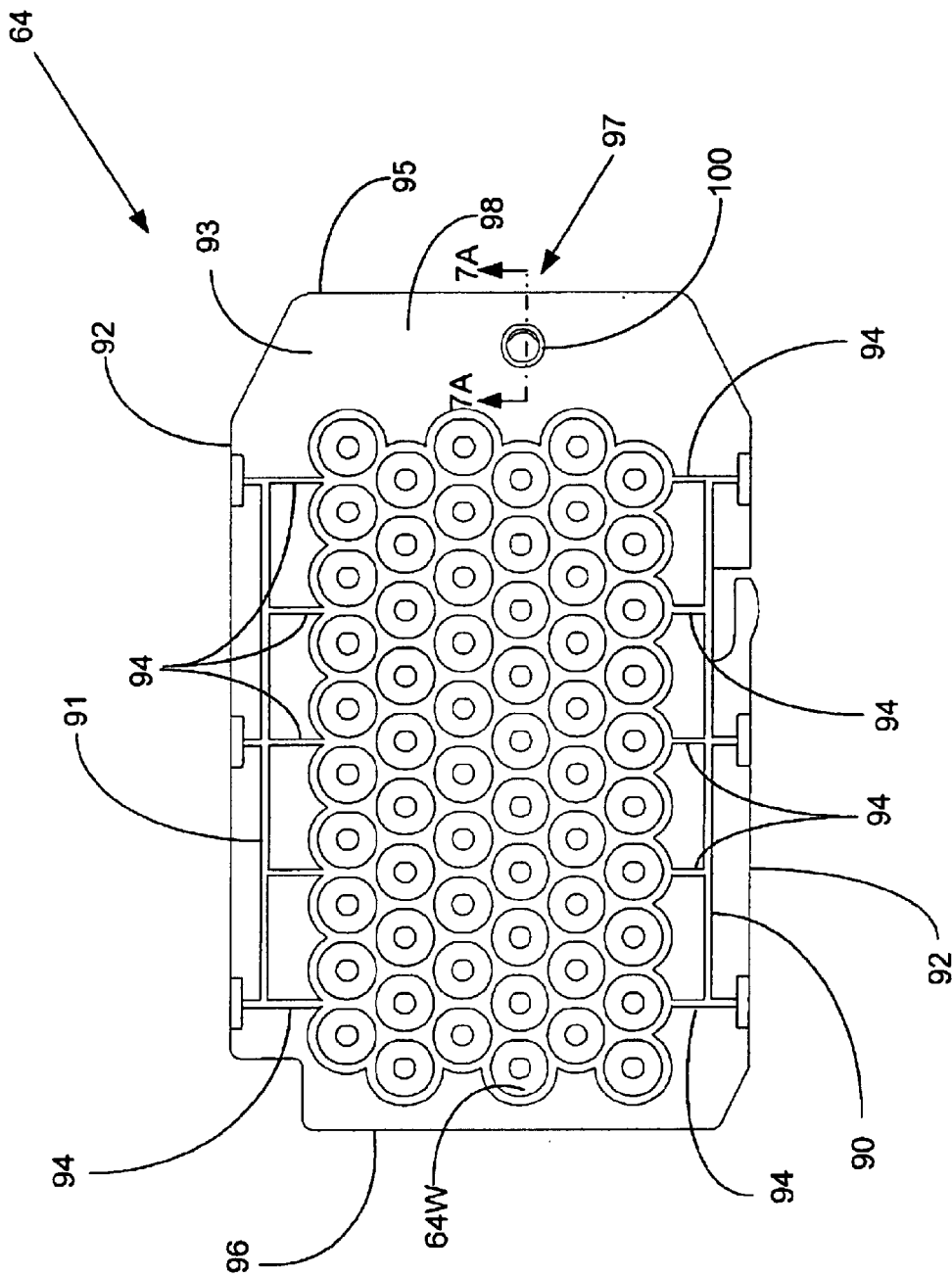

METHOD FOR MIXING LIQUID SAMPLES USING A LINEAR OSCILLATION STROKE

FIELD OF THE INVENTION

The present invention relates to a method and apparatus for uniformly mixing sample liquids, reagents or other solutions. In particular, the present invention provides a method for rapidly and uniformly mixing a liquid in a container by generating a sinusoidal mixing action of the container.

BACKGROUND OF THE INVENTION

Automated microbiology and clinical chemistry analyzers identify the presence of microorganisms and analytes in body fluids such as urine, blood serum, plasma, cerebrospinal fluid, sputum and the like. Automated microbiology and clinical chemistry analyzers improve productivity and enable the clinical laboratory to meet the workload resulting from high-test volume. Automated systems provide faster and more accurate results as well as valuable information to clinicians with regard to the types of antibiotics or medicines that can effectively treat patients diagnosed with infections or diseases. In a fully automated analyzer, many different processes are required to identify microorganisms or analytes and an effective type of antibiotic or medicine. Throughout these processes, patient sample liquids and samples in combination with various liquid reagents and antibiotics, are frequently required to be mixed to a high degree of uniformity producing a demand for high speed, low cost mixers that occupy a minimal amount of space.

Analyzers like those described above perform a variety of analytical processes upon microbiological liquid samples and in most of these, it is critical that a patient's biological sample, particularly when in a liquid state, be uniformly mixed with analytical reagents or diluents or other liquids or even rehydrated compositions and presented to an analytical module in a uniformly mixed state. In a biochemical analyzer, other liquids like broth may need to be uniformly stirred before being used. Various methods have been implemented to provide a uniform sample solution mixture, including agitation, mixing, ball milling, etc. One popular approach involves using a pipette to alternately aspirate and release a portion of liquid solution within a liquid container. Magnetic mixing, in which a vortex mixing action is introduced into a solution of liquid sample and liquid or non-dissolving reagents, herein called a sample liquid solution, has also been particularly useful in clinical and laboratory devices. Typical of such mixing is disclosed in U.S. Pat. No. 6,382,827 wherein a liquid solution in a liquid container is mixed by causing a freely disposed, spherical mixing member to rapidly oscillate within the solution in a generally circular pattern within the container. The spherical mixing member is caused to rapidly move within the solution by revolving a magnetic field at high speed in a generally circular pattern in proximity to the liquid container. Magnetic forces acting upon the magnetic mixing member cause it to generate a mixing motion within the liquid solution.

Ultrasonic mixing techniques like described in U.S. Pat. No. 4,720,374 employ ultrasonic energy applied from the exterior of the package and coupled into a reaction compartment so that a solid tablet of material within the compartment is dissolved or so that liquids contained therein are uniformly mixed. The container may include an array of sonication-improving projections mounted therein and spaced from each other to provide recirculating channels which communicate with both the tablet-receiving recess and the remainder of the volume of the container such that, in use, the projections act to confine a tableted material within a relatively high ultrasonic energy zone and simultaneously permit a flow of hydrating liquid from the high energy zone through the channels thereby to rapidly effect the dissolution of the tableted material.

U.S. Pat. No. 6,382,827 mixes a liquid solution contained in a liquid container by causing a freely disposed, spherical mixing member to rapidly oscillate within the solution in a generally circular pattern within the container. The spherical mixing member is caused to rapidly move within the solution by revolving a magnetic field at high speed in a generally circular pattern in proximity to the liquid container. Magnetic forces acting upon the magnetic mixing member cause it to generate a mixing motion within the liquid solution.

U.S. Pat. No. 5,824,276 cleans contact lens by applying a solution flow in an oscillatory fashion, so that the lens moves up and down within a container but does not contact the container for an extended time period. The method includes suspending the article in a solution within a container such that the article does not experience substantial or extended contact with the container interior. A predetermined flow of solution is passed into the container, thereby providing an upward force which, in conjunction with the buoyancy force, overcomes the downward gravitational force on the article, when the article is more dense than the solution. Alternatively, if the article has a lower density than the treatment solution, the flow is generated at the top of the container, to produce a substantially steady state effect.

Accordingly, from a study of the different approaches taken in the prior art to the problems encountered with mixing of small volume solutions taken with the challenges of minimizing the physical size of a magnetic mixer, there is a need for an improved approach to the design of a simplified, space-efficient liquid sample and or sample-reagent mixer. In particular, there is a need for a mixer which enables rapid and uniform mixing of liquid solutions contained in one or more wells in a multi-well tray or of liquid solutions contained in tubes held in a sample tube rack without mechanisms to move the tray or tubes to a separate location for mixing. There is a further need for a method for liquid mixing that is of such high speed that multiple mixing processes may be achieved without adversely affecting the time required for liquid solution analysis. There is a even further need for a method for mixing device having a mixing motion that is unidirectional so as to positively affect the cost reduction of liquid solution analysis.

SUMMARY OF THE INVENTION

Many of these disadvantages to the prior art are overcome by using the methods of this invention. This invention provides a method for generating a vortex-like mixing action within a liquid held in a container by causing the container to move back and forth in a constant sinusoidal pattern at high speeds. Momentum forces acting upon the liquid solution cause it to generate an internal mixing motion of the liquid solution without the aid of extraneous mixing members. The stroke and frequency may be optimized depending upon the geometrical sizes of the container.

BRIEF DESCRIPTION OF THE DRAWINGS

The invention will be more fully understood from the following detailed description thereof taken in connection with the accompanying drawings which form a part of this application and in which:

FIG. 1 is a schematic plan view of a single conventional automated clinical analyzer like those known in the art;

FIG. 2 is an enlarged partial schematic plan view of the automated analyzer of FIG. 1;

FIG. 7 is a plan view of an aliquot vessel array useful in practicing the present invention;

DETAILED DESCRIPTION OF THE INVENTION

Figure 3A:
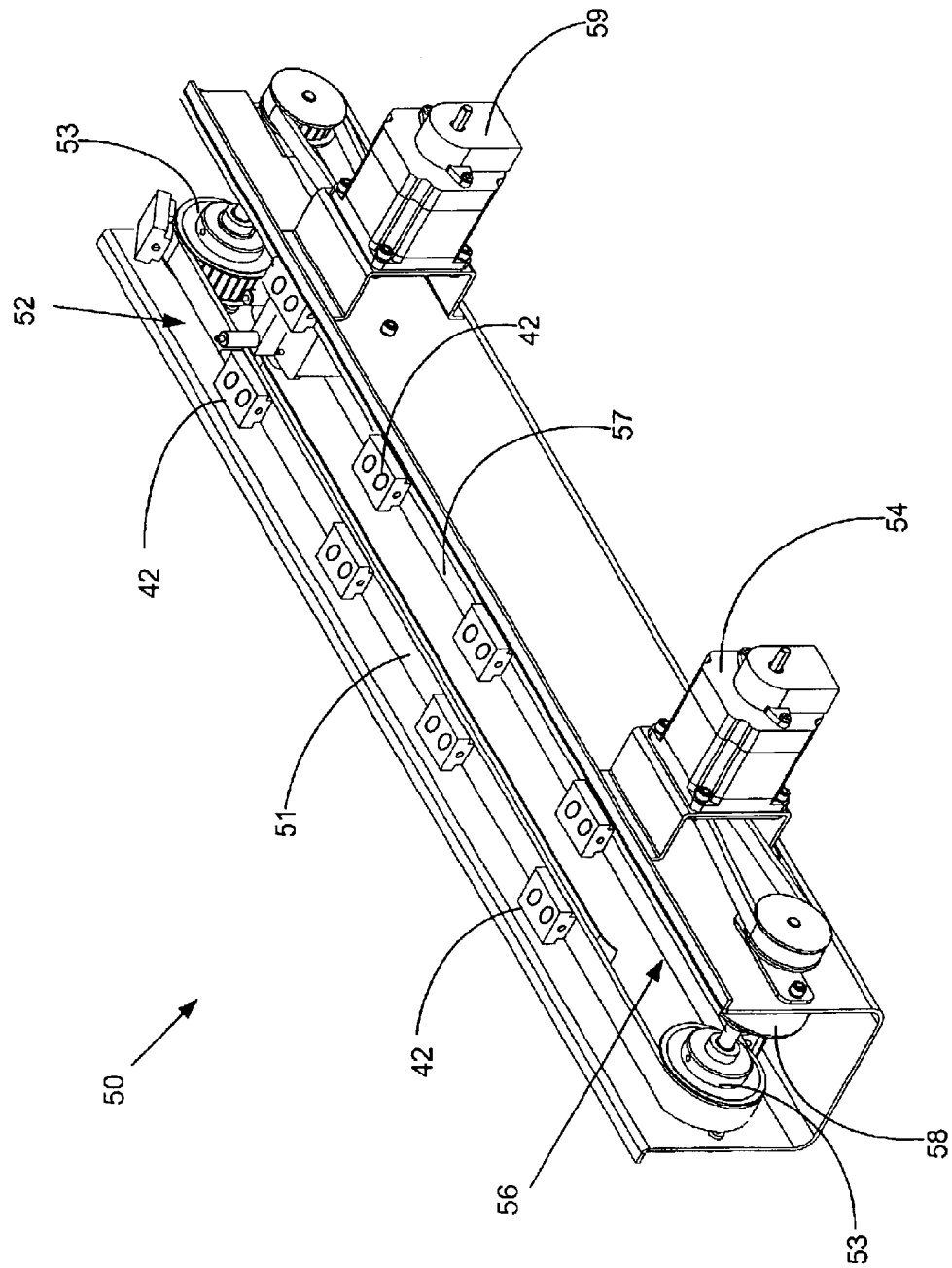
FIGS. 3A and 3B are perspective views of a sample rack transport system useful in the analyzer of FIG. 1.

FIG. 1, taken with FIG. 2, shows schematically the elements of a single convention automatic chemical analyzer 10 convenient for practicing the present invention and comprising a reaction carousel 12 supporting a outer cuvette circle 14 of cuvette ports 20 and an inner cuvette circle 16 of cuvette ports 22, the outer cuvette circle 14 and inner cuvette circle 16 being separated by a open groove 18. Cuvette ports 20 and 22 are adapted to receive a plurality of reaction cuvettes 24 typically formed as small, flat walled, U-shaped containers with an open central reaction portion closed at the bottom and with an opening at the top of cuvettes 24 to allow the addition of reagent and sample liquids. Reaction carousel 12 is rotatable using stepwise movements in a constant direction at a constant velocity, the stepwise movements being separated by a constant dwell time during which dwell time, carousel 12 is maintained stationary and an assay operation device 32 located proximate carousel 12 may operate on an assay mixture contained within a cuvette 24.

Two temperature-controlled reagent storage areas 26 and 28 each store a plurality of reagent cartridges 30, cartridges 30, for example being a multi-compartmented reagent container like those described in U.S. Pat. No. 4,720,374, or co-pending application Ser. No. 09/949,132 assigned to the assignee of the present invention, and sold under the tradename FLEX(tm) cartridge by Dade Behring Inc, Deerfield, Ill., and containing reagents as necessary to perform a given assay. A selectively-opened lid (not shown) covers each of reagent storage areas 26 and 28 to allow access to cartridges 30; for simplicity, only three reagent cartridges 30 are schematically illustrated in FIG. 2 as disposed beneath a cut out portion of reagent storage area 26 however similar reagent cartridges 30 are disposed within reagent storage area 28. Shuttle means (not shown) move individual cartridges 30 to access ports for conventional reagent aspiration and dispense probes 27 and 29. As shown, storage area 28 may be conveniently located external to the circumference of outer cuvette circle 14 and reagent storage area 26 may be conveniently located internal to the circumference of inner cuvette circle 16.

A clinical analyzer 10 like those on which the present invention may be performed has a plurality of conventional assay operation devices 32 disposed proximate carousel 12 and at which are positioned individual computer controlled electromechanical devices, such as sensors, reagent add stations, mixing stations, and the like, as required to perform the myriad of actions required in well known clinical assays. Such devices and their operation are well known in the art and need not be described herein. See, for example, U.S. Pat. Nos. 5,876,668, 5,575,976 and 5,482,861 and the references cited therein.

An indexing drive for the reaction carousel moves the reaction vessels in the constant direction a predetermined numbers of incremental steps. The length of the circumference of cuvette circles 14 and 16, the separation distance between cuvette ports 20 and 22, the number of cuvette ports 20 and 22, and the number of increments per indexing are selected so that any given cuvette ports 20 and 22 returns to its original starting position after a fixed number of incremental steps. Thus, all cuvette ports 20 and 22 on the reaction carousel 12 return to their original location in a full operational cycle time which is determined by the fixed number of incremental steps multiplied by the sum of dwell time at each assay device and the time required for a stepwise movement.

Incoming sample specimens to be tested are contained in sample tubes 40 mounted in sample tube racks 42 and transported into the arc of a conventional liquid sampling arm 44, for example, by a bi-directional incoming, as indicated by open arrow 36A, and outgoing, as indicated by open arrow 36B, sample tube transport system 36, described in U.S. Pat. No. 6,571,934 assigned to the assignee of the present invention. A magnetic drive system 50 useful in analyzer 10 is seen in the perspective drawing FIG. 3A as having at least one bi-directional linear drive transport mechanism 52 comprising, for example, a first belt 51 endlessly circulating around a pair of first pulleys 53, one of the first pulleys 53 being coupled to a first bi-directional motor 54, the first belt 51 and first pulleys 53 being mounted beneath and in close proximity to the operating surface of analyzer 10 which defines input and output lanes. In an exemplary embodiment of the present invention only a single incoming sample tube transport system 50 is employed and only a single bi-directional linear drive transport mechanism 52 is required. It should be understood that any of several mechanisms are capable of providing the bi-directional linear drive transport mechanism 52 used within the present invention, for instance a bi-directional motor coupled to a linear drive screw, or a pneumatic operated plunger, both supporting the magnetic housings and having a magnet therein.

Figure 3B:
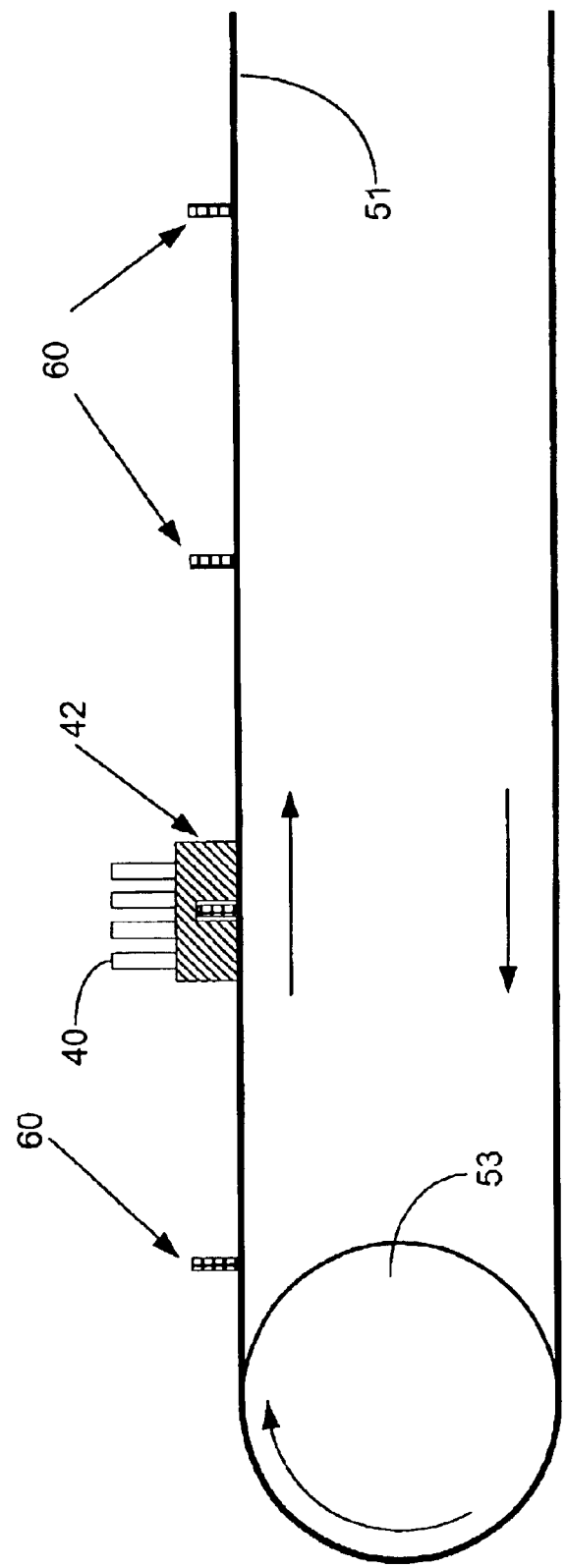

Alternately, first belt 51 may driven by motor 54 only in an incoming direction, for example along the direction of arrow 36A. In a similar manner, magnetic drive system 50 may additionally comprise a second belt 57 endlessly circulating around a pair of second pulleys 58, one of the second pulleys 58 (only one such second pulley 58 is visible) being coupled to a second bi-directional motor 59, the second belt 57 and second pulleys 58 being mounted beneath and in close proximity to the output lane portion of the operating surface of analyzer 10, indicated by open arrow 36B. Second belt 57 is driven by second motor 59 in an outgoing direction 36B opposite to the incoming direction 36A. Motors 54 and 59 are typically stepper motors independently controlled by computer 15 and have drive gears coupled to pulleys 53 and 58 which are preferably formed as pulley gears interlaced with gear teeth formed on belts 51 and 57. The magnetic drive system 50 is described here in terms of a pulley-and-belt drive mechanism, however, any of a number of bi-directional linear drive mechanisms may be employed to achieve the purpose of linearly moving a sample tube rack 42 in either of two opposing directions. FIG. 3B illustrates a plurality of sample tube racks 42 magnetically coupled to each drive belt 51 and 57 by means of a plurality of upright posts 59 generally equally spaced apart by a predetermined distance, and, as seen in FIG. 3B, the plurality of upright posts 60 are attached to belts 51 and 57 at that same predetermined distance. Posts 60 are adapted by any of various mechanical techniques, such as screws, snaps, welds, etc., to secure the plurality of magnetic sample tube racks 42 to belt 51 and 57.

Figure 4:
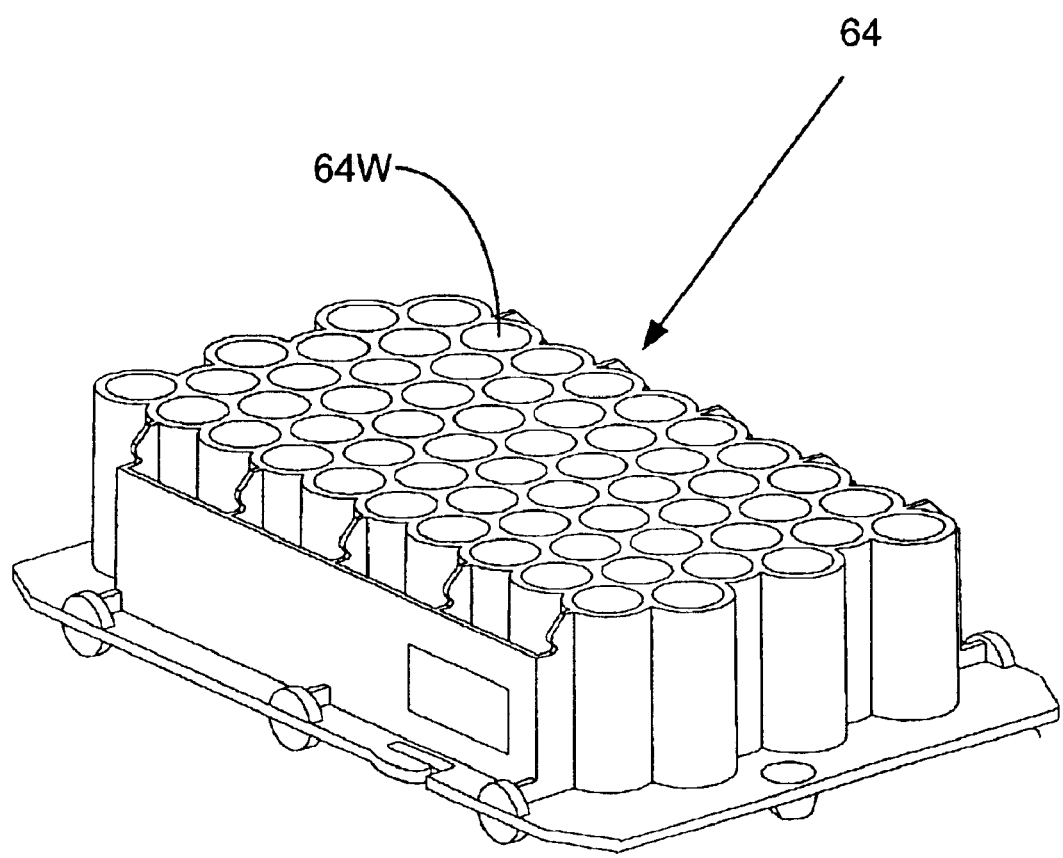
FIG. 4 is a perspective view of a multi-well aliquot vessel useful in practicing the present invention.

A fluid sampling arm 44 supports a conventional liquid sampling probe 46 and is mounted to a rotatable shaft 48 so that movement of sampling arm 44 describes an arc intersecting the sample tube transport system 36 and an aliquot strip transport system 62 described later and adapted to transport multi-well aliquot vessels 64, like that seen in FIG. 4, to a conventional sample/reagent aspiration and dispense arm 66 located proximate reaction carousel 12. Sampling arm 44 is operable to aspirate liquid sample from sample tubes 40 and to dispense a sample aliquot portion into one or more of a plurality of aliquot wells 62W in aliquot vessels 62, depending on the quantity of sample required to perform the requisite assays and to provide for a sample aliquot to be retained by analyzer 10 within an environmental chamber 38. Sample/reagent aspiration and dispense arm 66 is controlled by computer 15 and is adapted to aspirate a controlled amount of sample from wells 52W via a conventional liquid probe 66P and to dispense an appropriate amount of aspirated sample into one or more cuvettes 24 for assay testing for one or more analytes. After sample has been dispensed into reaction cuvettes 24 in cuvette ports 20 and 22, conventional transfer means move aliquot strips 52 as required between aliquot strip transport system 50 and an environmental chamber 38 as described in co-pending application Ser. No.: 10/773,079 also assigned to the assignee of the present invention, or, optionally, to a waste disposal area, not shown. Patient liquid specimens contained in open sample tubes 40 are identified by reading bar coded indicia placed thereon using a conventional bar code reader to determine, among other items, a patient's identity, the tests to be performed, if a sample aliquot is desired to be retained inside environmental chamber 38 and if so, for what period of time. It is also common practice to place bar coded Indicia on sample tube racks 42 and employ a large number of conventional bar code readers installed throughout analyzer 10 in order to ascertain, control and track the location of both sample tubes 40 and sample tube racks 42. Such reader devices and the techniques for tracking are well known in the art and are not seen in FIG. 1 nor need be discussed further.

Analyzer 10 is controlled by computer 15 based on software written in a machine language, like that used on the Dimension® clinical chemistry analyzer sold by Dade Behring Inc, of Deerfield, Ill., and widely used by those skilled in the art of computer-based electromechanical control programming. At least two reagent aspiration and dispense arms 27 and 29 comprising a pair of conventional liquid reagent aspiration and dispense probes, 27P and 29P, respectively, are independently mounted and translatable between reagent storage areas 26 and 28, respectively. Probes 27P and 29P are shown in FIG. 1 in two operating positions, with one probe, 29P, adapted to remove reagent from a reagent container in storage area 28 and to dispense aspirated reagent into cuvettes 22 and 24 located in cuvette circles 14 and 16 and with the other probe, 27P, adapted to remove reagent from a reagent container in storage area 26 and to dispense aspirated reagent into cuvettes 22 and 24 located in cuvette circles 14 and 16. Probes 27P and 29P typically comprise an ultrasonic mechanism used for hydrating, aspirating, dispensing and mixing reagents. The hydrating, aspirating, dispensing and mixing mechanisms have features well known in the art and need not be described further.

Cuvette load and unload stations 61 and 63 are positioned proximate outer cuvette carousel 14 and are conventionally adapted to load cuvettes 24 into cuvette ports 20 and 22 seen in FIG. 2 formed in outer cuvette carousel 14 and inner carousel 16 using for example a translatable robotic clamp 64. Conventional sample processing devices 32 (FIG. 2), are positioned at selected circumferential locations about the reaction carousel 12 in order to access reaction cuvettes 24. Processing devices 32 are adapted to provide, among other processing steps, for mixing together of the sample liquid and the reagent liquid contained in cuvettes 24, for washing the sample liquid and the reagent liquid contained in cuvettes 24, and for magnetic separation of tagged magnetic particles from free tags or reagent liquid contained in cuvettes 24.

Various assay analyzing stations 67 may be located proximate outer reaction carousel 12 and are adapted to measure light absorbence in or emission from cuvettes 24 at various wavelengths, from which the presence of analyte in the sample liquid may be determined using well-known analytical techniques. Stations 67 typically comprise conventional photometric, fluorometric or luminescent measuring devices adapted to perform an interrogating measurement at any convenient time interval during which reaction carousel 12 is stationary.

Drive means are provided for independently rotating outer reaction carousel 12 about an axis, the drive means typically comprising gear teeth disposed on the carousel 12 and interlacing with pinion gears mounted on the shaft of a motor. The drive means may be of conventional design and are not illustrated.

Figure 5:
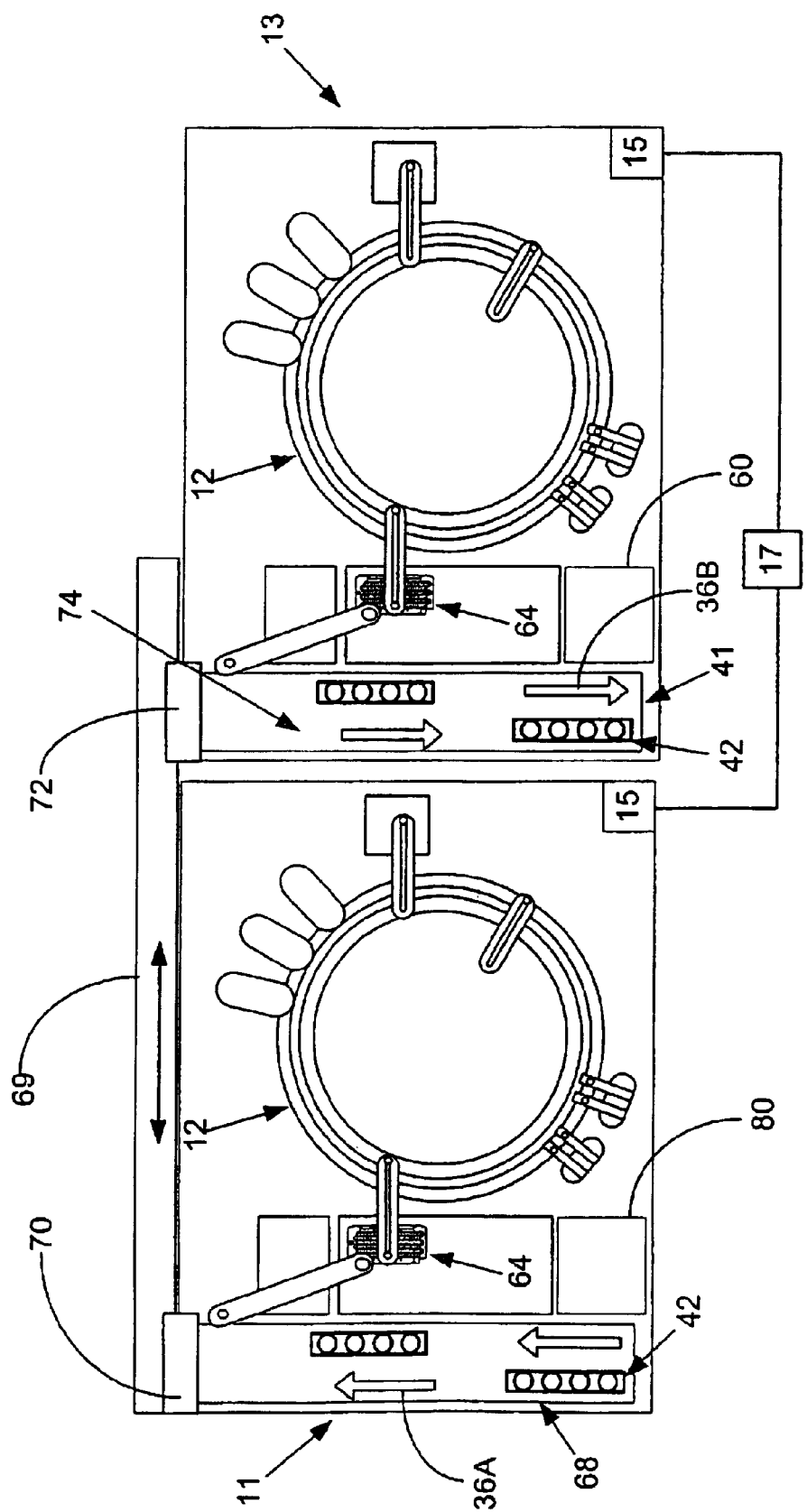
FIG. 5 is schematic plan view of a pair of automated clinical analyzers like those of FIG. 1, useful in practicing the present invention.

FIG. 5 illustrates a method for operating a pair of automatic clinical analyzers like analyzer 10 seen in FIG. 1, identified as analyzers 11 and 13, linked together by a bi-directional sample rack shuttle 69 that optimizes sample assay throughput irregardless of the mix of different assays required to be performed for different samples to be tested as described in co-pending application Ser. No.: 10/373,297 also assigned to the assignee of the present invention. In this instance, the individual computers 15 of analyzers 10 may be cooperatively controlled by a stand-alone computer 17 so programmed using well known techniques, or a single one of the computers 15 may alternately be programmed so as to control both analyzers 10 and 11.

Analyzers 11 and 13 are essentially identical to one another except that the menu of assays capable of being performed thereon is selectively different as explained later. For convenience in describing operation of the pair of automatic clinical analyzers 10, the leftmost analyzer is identified an analyzer 11 and the rightmost is identified as analyzer 13. In this arrangement, the bi-directional incoming and outgoing sample tube transport system 36 of the analyzer 10 of FIG. 1 is converted into a one-way incoming sample tube transport system 68, indicated by open arrow 36A, adapted to receive all sample tube racks 42 having all sample tubes 40 to be analyzer by either analyzer 11 or 13. Any sample tube rack 42 may then be transferred from incoming sample tube transport system 68 by a conventional tube rack transfer mechanism 70 operable between analyzer 10 and bi-directional sample rack shuttle 69 and shuttled from sample rack shuttle 66 via another conventional tube rack transfer mechanism 72 onto analyzer 13 as directed by computer 17. In this arrangement, the sample tube transport system 36 of analyzer 11 may be converted into a one-way outgoing transport system 74, indicated by open arrow 36B, adapted to dispose of all sample tube racks 42 having sample tubes 40 with samples finally analyzed by either analyzer 11 or 13. Operation and features of a transport mechanism like sample rack shuttle 69 are well known in the art, for example as discussed in U.S. Pat. Nos. 6,117,392 and 6,117,683 and 6,141,602, and are thus not provided here. Generally, conveyor belts, hooks, magnetic devices, or the like may be employed in the design of shuttle 69, tube rack transfer mechanisms 70 and 72 and transport systems 68 and 74.

Figure 6:
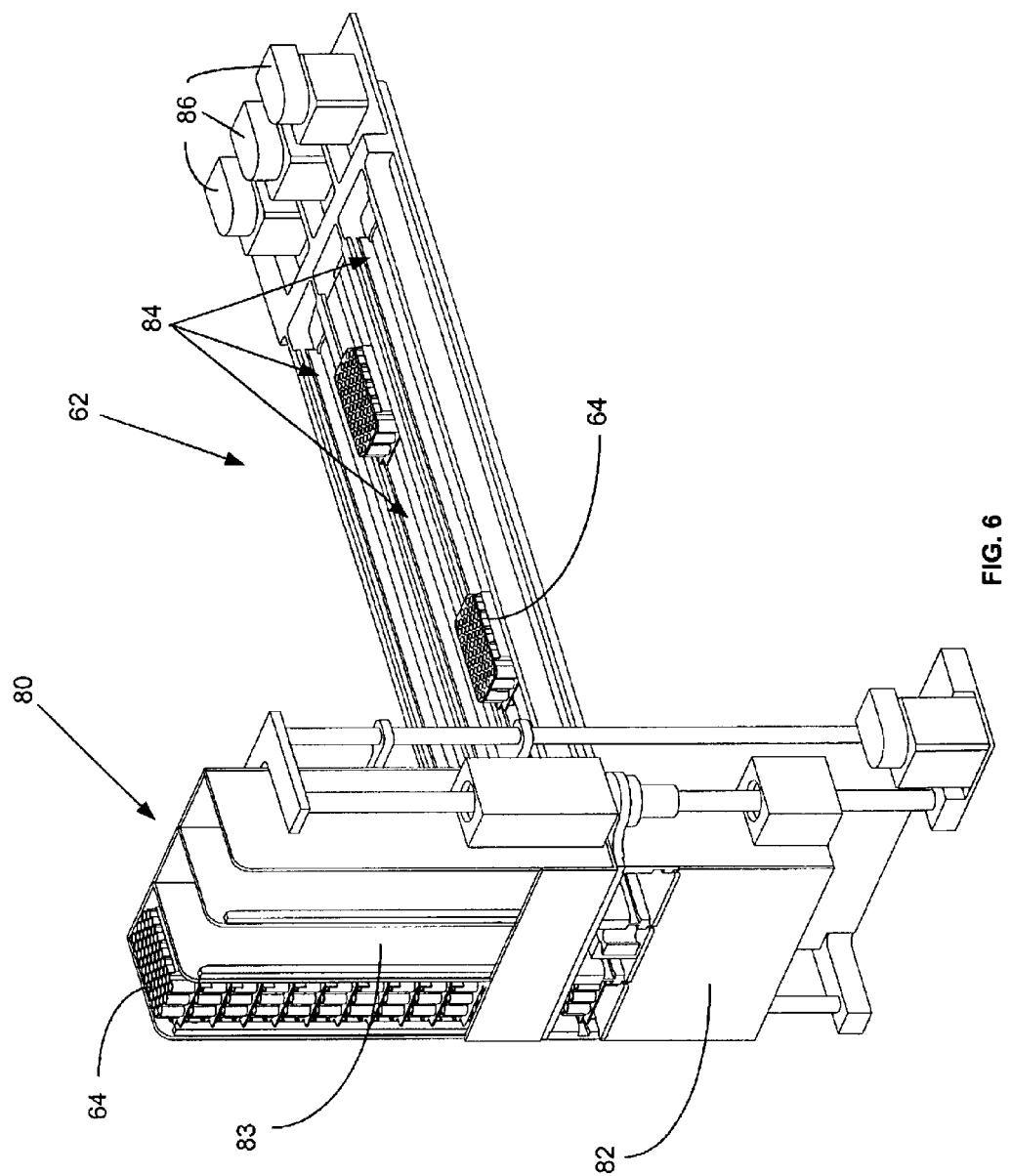
FIG. 6 is a perspective view of an automated aliquot vessel array storage and handling unit integrated with a sampling track in which the present invention may be practiced to advantage.
Figure 6A:
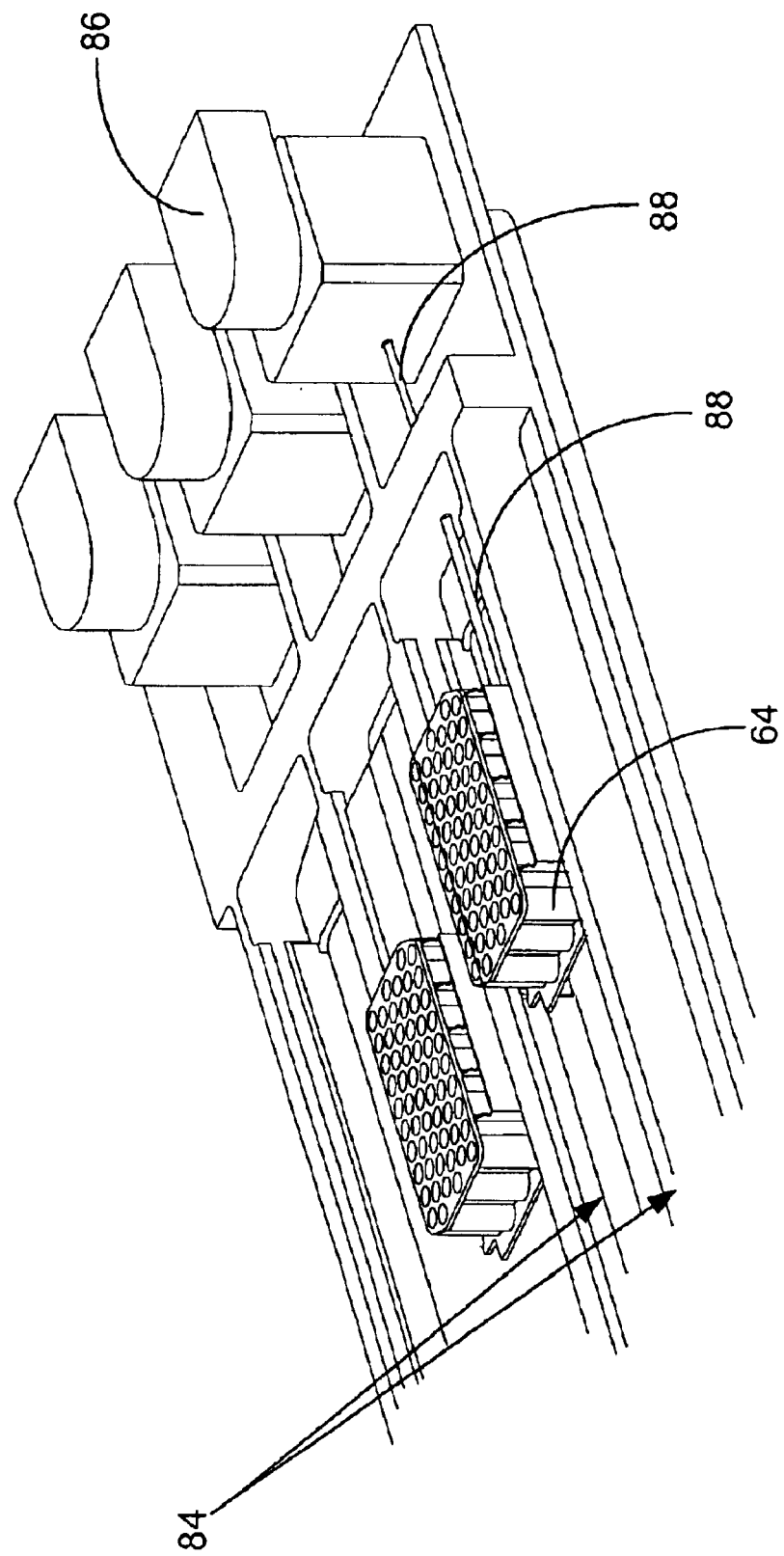
FIG. 6A is an enlarged perspective view of a portion of the automated aliquot vessel array storage and handling unit of FIG. 6 illustrating one embodiment of the present invention.

As seen in FIG. 6, an automated aliquot vessel array storage and handling unit 80 is disposed proximate aliquot strip transport system 62 and is adapted in a manner so that aliquot vessel arrays 64 may be automatically transferred from a vertically translatable array elevator 82 from any of three aliquot vessel array inventory shafts 83 within aliquot vessel array storage unit 80 onto one of several pairs of parallel aligned aliquot vessel array sampling tracks 84. Aliquot vessel arrays 42 are mounted within aliquot vessel array storage unit 80 between pairs of sampling tracks 84 having flared open ends suitable for discharging and receiving an aliquot vessel array 42. Two aliquot vessel arrays 42 are seen located between a pair of sampling tracks 84. The lengthwise positioning of an aliquot vessel array 42 between sampling tracks 84 is provided by a rotary step motor 86 adapted to independently move aliquot vessel arrays 42 in either direction between a pair of sampling tracks 84, the motors 86 being connected for example by a connecting rod 88 to each aliquot vessel array 42 (as seen in FIG. 6A). Each aliquot vessel array 64 has a protruding and downwardly projecting zero-backlash hitch 100 described hereinafter adapted to secure aliquot vessel array 64 to a pin portion 101 of connecting rod 88.

Figure 7A:
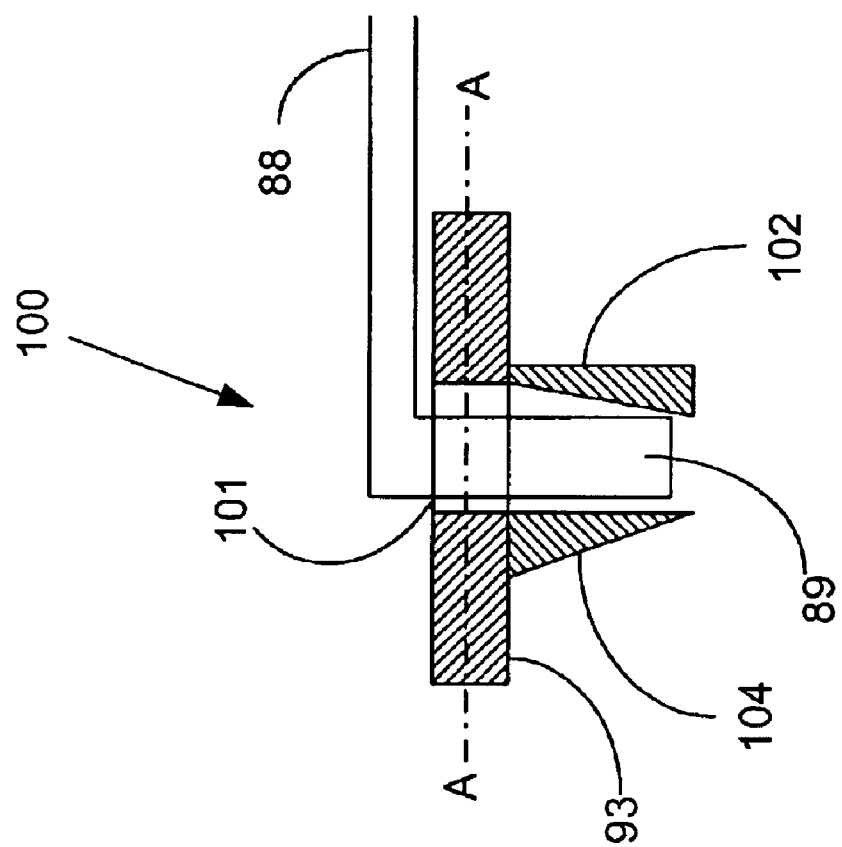
FIG. 7A is a sectional view taken along the line 7A—7A of a portion of the aliquot vessel array of FIG. 7 and looking in the direction of the arrows; and, FIG. 8 is an perspective view of a portion of an alternate embodiment of the present invention.

FIG. 7 is a plan view of the aliquot vessel array 64 useful in practicing a first embodiment of the present Invention showing spatial relationships between parallel first and second side wails 90 and 91 extending lengthwise along the longer orthogonal edges 92 of a generally rectangular aliquot base plate 93. An ordered array of open wells 64W is formed between the pair of parallel side walls 90 and 91, and separated therefrom by notched side flanges 94. Front orthogonal edge 95 and rear orthogonal edge 96 of base plate 116 are further seen to be formed mutually parallel to one another with a zero-backlash hitch 100 formed in the central region 97 of the front shorter perimeter portion 98 between the array of open wells 64W and front orthogonal edge 95. An important feature of the aliquot vessel array 64 is the zero-backlash hitch 100 formed in the central region 97 of the front shorter perimeter portion 98 between the shorter orthogonal edge 95 and the array of open wells 64W. Sectional line 7A—7A in FIG. 7A is enlarged to show details of zero-backlash hitch 100 comprising an opening 101 in base plate 93 and a pair of semi-circular sleeves extending downwardly, a frontal sleeve 102 formed to slant backwards from the front of aliquot vessel array 64 towards a rear sleeve 104 formed generally perpendicularly to base plate 93. The pair of semi-circular sleeves 102 and 104 are spaced apart a distance so that a downwardly descending finger-latch portion 89 of connecting rod 88 may be inserted between the frontal sleeve 102 and rear sleeve 104 in such a manner that the backwards slanting frontal sleeve 102 biases finger-latch portion 89 securely against rear sleeve 104, thereby ensuring that aliquot vessel array 42 may be accurately positioned within track 84 and secured to motor 86. The backwards slanting frontal sleeve 102 provides zero-backlash locations to aliquot vessel array 64 throughout a repeated number of movements in both directions between tracks 84. Aliquot vessel array 64 is repeatedly moved to a single sampling location in track 84 whereat multiple aliquots of sample are aspirated from wells 64W, wells 64W being environmentally sealed with a conventional laminate covering (not shown) and punctured by an aspiration needle. It is important that aliquot vessel array 64 be accurately positioned within track 84 by zero-backlash hitch 140 so that only a single aspiration puncture is made in the laminate covering during multiple sample aspirations thereby minimizing sample evaporation losses during subsequent storage of the aliquot vessel array 102.

An important and surprising discovery of the present invention is that a vortex-like mixing action may be generated within a liquid contained in wells 64W of aliquot vessel array 64 by high speed linear movements in opposite directions of aliquot vessel array 42 between sampling tracks 84. It has been found that such bi-directional movement along a linear path, like that defined by sampling tracks 84 is highly effective in thoroughly mixing liquid sample and reagents and/or re-suspending a liquid mixture of different liquid constituents. It has further been found that the optimum length of such bi-directional linear movements and the frequency at which the direction of movement is changed are dependent upon the diameter of well 64W or other larger container like that shown in FIG. 8.

In a first operational example of the present invention, a red liquid with specific gravity slightly greater than 1.0 is placed into the bottom of wells 64W. The red liquid is then covered with a layer of water resulting in a stratified sample, red liquid on the bottom with clear water on the top. In this example, wells 64W are approximately 2–3 mm in diameter and about 1 cm in depth. Stepper motor 86 is operated so as to provide a bi-directional constant linear stroke in a stroke of about 3–6 millimeters at a constant frequency in a range of frequencies varying between about 10 to 40 Hz. Consequently, aliquot vessel array 64 is moved in a constant sinusoidal pattern selected from the range of sinusoidal patterns comprising 3–6 millimeters and frequencies varying between about 10 to 40 Hz. Examination of the fluid in wells 64W discloses that in the frequency ranges between about 10–15 Hz and between about 30–40 Hz, very little suspension or mixing of the red liquid occurs within the water sample. However, when the stepper motor 86 is operated so that aliquot vessel array 42 is moved with bi-directional linear stroke of 3–6 millimeters in a range of frequencies varying between about 20 to 30 Hz, a uniform suspension or mixing of the red liquid occurs within the water sample in a time period of about 1–3 seconds.

Figure 8:
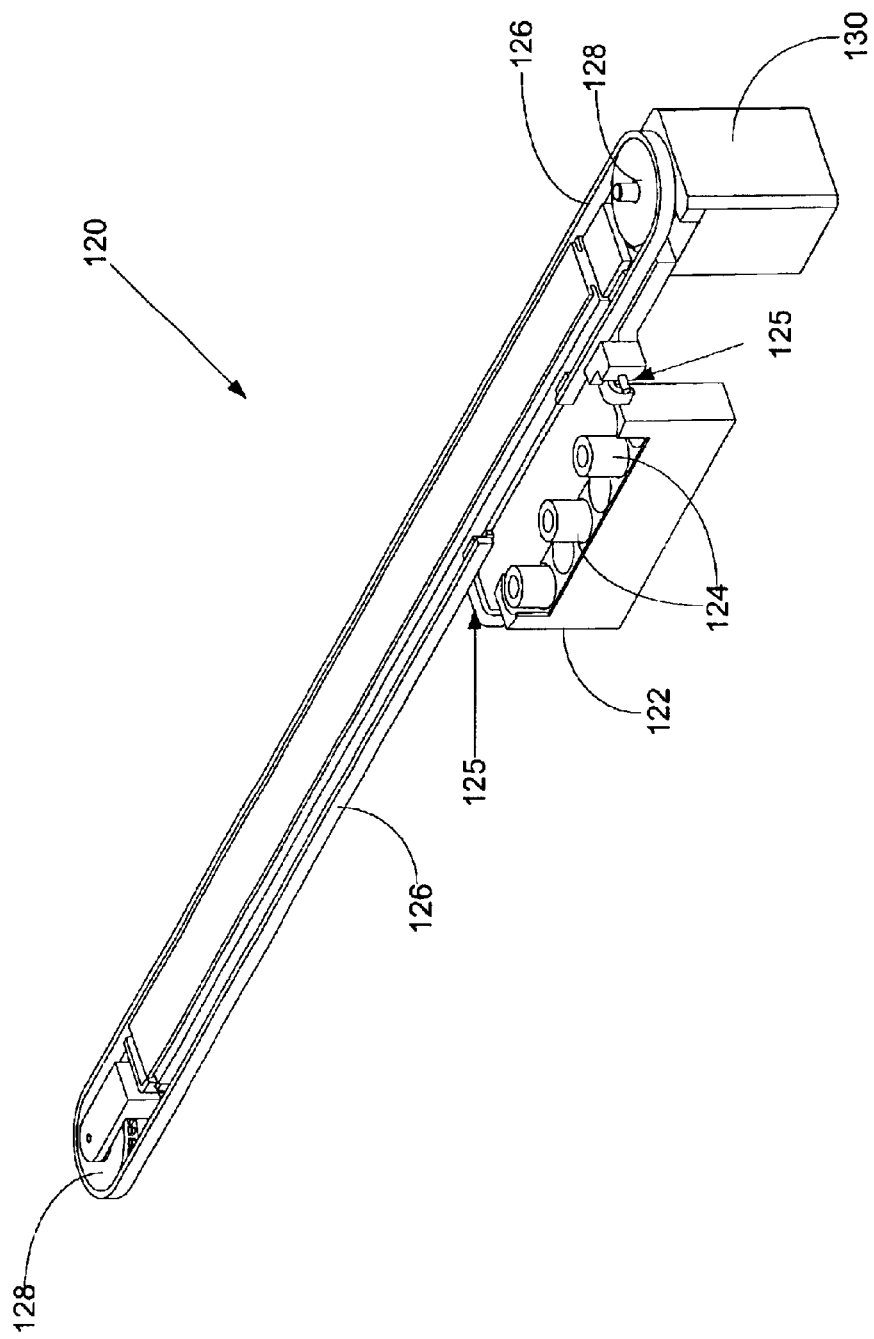

In an alternate operational example of the present invention depicted in FIG. 8, liquid water colored with red food dye is placed into reagent containers 124 supported in a reagent tray 122, the reagent tray 122 being suspended by a pin-and slotted lever 125 from a flexible belt 126. In this example, reagent containers 124 are approximately 10–15 mm in diameter and about 2 cm in depth. Reagent containers 124 are allowed to remain stationary until the dye settles to the bottom of the reagent containers 124 and the water is clear. Flexible belt 126 is seen as being driven by a pair of pulleys 128, one pulley 128 of which is mounted to stepped motor 130. Stepper motor 130 is operated so as to provide a bi-directional constant linear oscillation of the reagent containers 124 supported in a reagent tray 122 in a stroke of about 8–12 millimeters at a constant frequency in a range of frequencies varying between about 10 to 40 Hz. Consequently, reagent containers 124 supported in a reagent tray 122 are moved in a constant sinusoidal pattern selected from the range of sinusoidal patterns comprising about 8–12 millimeters stroke and frequencies varying between about 5 to 40 Hz. Examination of the fluid in reagent containers 124 discloses that in the frequency ranges between 5–10 Hz and between about 15–40 Hz, very little re-suspension or mixing of the red dye occurs within the water sample. However, when the stepper motor 86 is operated so that reagent containers 124 are moved with bi-directional linear stroke of 8–12 millimeters in a range of frequencies varying between about 10 to 15 Hz, a uniform re-suspension or mixing of the red dye occurs within the water sample in a time period of about 1–3 seconds.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. A method for mixing a liquid held within a well having a first diameter by moving the well in a first linear oscillation stroke at a first frequency or by moving the well at a second frequency in a second linear oscillation stroke if the well has a second diameter, the second diameter being about one-fifth the first diameter, the second frequency being about twice the first frequency and wherein the second linear oscillation stroke is about one-half the first linear oscillation stroke.

2. The method of claim 1 wherein the first diameter is about 10–15 mm, the first frequency is between about 10 to 15 Hz and the linear oscillation stroke is between 8–12 mm.

3. The method of claim 1 wherein the second diameter is about 2–3 mm, the second frequency is between about 20 to 30 Hz and the linear oscillation stroke is between 3–6 mm.

4. The method of claim 1 wherein the well is one of an array of wells formed in an aliquot vessel array having a zero-backlash hitch and wherein moving the well comprises moving the aliquot vessel array repeatedly in both directions between a pair of tracks.

5. The method of claim 1 wherein the mixing is conducted for a time period of about 1–3 seconds.

6. A method for mixing a liquid held within a well if the well has a first depth by moving the container in a first linear oscillation stroke at a first frequency or by moving the container in a second bi-directional linear oscillation stroke at a second frequency if the well has a second depth, the second depth being about one-half the first depth, and the second frequency being about twice the first frequency and wherein the second linear oscillation stroke is about one-half the first linear oscillation stroke.

7. The method of claim 6 wherein the first depth is about 2 cm and the first frequency is between about 10 to 15 Hz.

8. The method of claim 6 wherein the well is one of a group of containers supported in a tray, the tray being suspended from a flexible belt driven by a pair of pulleys, one pulley of which is mounted to a stepper motor adapted to provide a linear oscillation of the tray.

9. The method of claim 6 wherein the mixing is conducted for a time period of about 1–3 seconds.

* * * * *